(12) United States Patent
Au et al.

(10) Patent No.: US 10,952,944 B2
(45) Date of Patent: Mar. 23, 2021

(54) CYCLOCARBOXYLIC ACID CONTAINING PERSONAL CARE COMPOSITIONS

(71) Applicant: Conopco, Inc., Englewood Cliffs, NJ (US)

(72) Inventors: Van Au, Oxford, CT (US); Bijan Harichian, Irvine, CA (US)

(73) Assignee: Conopco, Inc., Englewood Cliffs, NJ (US)

( * ) Notice: Subject to any disclaimer, the term of this patent is extended or adjusted under 35 U.S.C. 154(b) by 12 days.

(21) Appl. No.: 15/773,355

(22) PCT Filed: Oct. 17, 2016

(86) PCT No.: PCT/EP2016/074855
§ 371 (c)(1),
(2) Date: May 3, 2018

(87) PCT Pub. No.: WO2017/080758
PCT Pub. Date: May 18, 2017

(65) Prior Publication Data
US 2018/0318190 A1    Nov. 8, 2018

(30) Foreign Application Priority Data
Nov. 10, 2015  (EP) .................................... 15193958

(51) Int. Cl.
| | | |
|---|---|---|
| *A61K 8/36* | (2006.01) | |
| *A61K 8/35* | (2006.01) | |
| *A61K 8/37* | (2006.01) | |
| *A61K 8/39* | (2006.01) | |
| *A61K 8/86* | (2006.01) | |
| *A61K 8/40* | (2006.01) | |
| *A61K 8/04* | (2006.01) | |
| *A61K 8/42* | (2006.01) | |
| *A61Q 17/04* | (2006.01) | |

(52) U.S. Cl.
CPC ............. *A61K 8/36* (2013.01); *A61K 8/042* (2013.01); *A61K 8/35* (2013.01); *A61K 8/361* (2013.01); *A61K 8/37* (2013.01); *A61K 8/39* (2013.01); *A61K 8/40* (2013.01); *A61K 8/42* (2013.01); *A61K 8/86* (2013.01); *A61Q 17/04* (2013.01); *A61K 2800/5422* (2013.01)

(58) Field of Classification Search
CPC combination set(s) only.
See application file for complete search history.

(56) References Cited

U.S. PATENT DOCUMENTS

| 4,847,072 | A | 7/1989 | Bissett et al. | |
|---|---|---|---|---|
| 2006/0120976 | A1 * | 6/2006 | Brown ...................... | A61K 8/34 424/59 |
| 2009/0028807 | A1 | 1/2009 | Giustiniani et al. | |
| 2012/0064136 | A1 | 3/2012 | Baker, Jr. | |
| 2013/0189204 | A1 | 7/2013 | Duggal et al. | |
| 2013/0266527 | A1 | 10/2013 | Duggal et al. | |
| 2014/0227212 | A1 | 8/2014 | Wagener et al. | |
| 2015/0290095 | A1 | 10/2015 | Balakrishnan et al. | |

FOREIGN PATENT DOCUMENTS

| CN | 101347389 | 1/2009 | |
|---|---|---|---|
| GB | 718454 | 11/1954 | |
| GB | 1127026 | 9/1968 | |
| WO | WO2008061658 | 5/2008 | |
| WO | WO 2014/139965 | * 9/2014 | ............... A61K 8/44 |
| WO | WO2014135360 | 9/2014 | |
| WO | WO2014152686 | 9/2014 | |
| WO | WO2015086428 | 6/2015 | |

OTHER PUBLICATIONS

Search Report and Written Opinion in EP15193958, dated Apr. 11, 2016.
Search Report and Written Opinion in PCTEP2016074855, dated Jan. 10, 2017.

* cited by examiner

*Primary Examiner* — Hasan S Ahmed
(74) *Attorney, Agent, or Firm* — Ellen Plotkin

(57) ABSTRACT

The present technology provides personal care compositions that include about 0.1 wt % to about 10 wt % of (Formula), or a mixture of any two or more thereof; wherein n is 0, 1, or 2; m is 1, 2, or 3; p is 0, 1, or 2; and q is 1, 2, or 3; about 0.1 wt % to about 30 wt % of a UV-B sunscreen oil; about 0.1 wt % to about 30 wt % of a nonionic surfactant of Formula I (I) where $R^1$ is a $C_6$-$C_{12}$ alkyl group; r is an integer from 6 to 13, and the nonionic surfactant has a hydrophilic-lipophilic balance of about 10 to about 14; and about 40 wt % to about 96 wt % of the personal care composition is water.

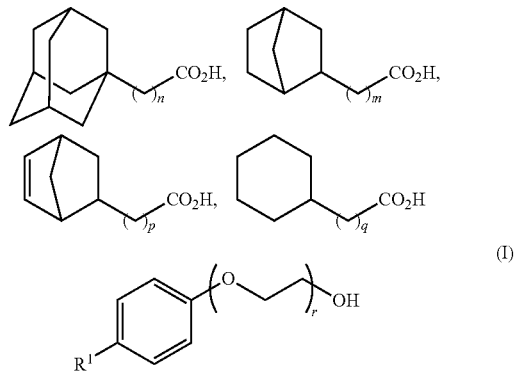

16 Claims, No Drawings

CYCLOCARBOXYLIC ACID CONTAINING PERSONAL CARE COMPOSITIONS

FIELD OF THE INVENTION

The present technology generally relates to personal care compositions including certain non-aromatic carboxylic acids and a UV-B sunscreen oil.

BACKGROUND OF THE INVENTION

Solar radiation includes about 5% ultraviolet (UV) radiation, wavelength of which is between 200 nm and 400 nm. It is further classified into three regions: from 320 to 400 nm (UV-A), 290 to 320 nm (UV-B) and from 200 to 290 nm (UV-C). A large part of UV-C radiation is absorbed by the ozone layer. Scientific studies have indicated that exposure to UV-A and UV-B radiation for short period causes reddening of the skin and localized irritation, whereas continued and prolonged exposure can lead to sunburn, melanoma and formation of wrinkles and age spots. It is also reported that UV radiation causes significant damage to hair. Therefore, it is desirable to protect the skin and other keratinous substrates of the human body from the harmful effects of both UV-A and UV-B radiation, in addition to increasing the SPF protection.

Various cosmetic preparations have been reported for preventing and/or protecting the skin from harmful effects of ultraviolet radiation. Numerous organic sunscreen agents capable of absorbing UV-A rays are reported in the field of cosmetics amongst which a particularly useful sunscreen is 4-tert-butyl-4'-methoxydibenzoylmethane (a.k.a. t-butylmethoxydibenzoylmethane or avobenzone, also sold as Parsol 1789). Many UV-B sunscreens are also known and approved for safe use in personal care compositions for protection from UV-B radiation. Many cosmetic manufacturers prefer to include both UV-A and UV-B sunscreens in photoprotective compositions so as to provide protection over the entire range of UV radiation.

Thus, cosmetic manufacturers aim to provide consumers with products having better and better sun protection. One of the ways of achieving this is to incorporate higher and higher levels of UV-A and UV-B sunscreens.

One disadvantage of this approach is the high cost associated with incorporation of high levels of sunscreens which are expensive. Further, there are safety and regulatory limitations on the upper limit of incorporation of these sunscreens. Finally, sensory and physical properties are also altered on incorporation of sunscreens, particularly when the amounts of sunscreens are increased, because organic sunscreens are oily, and thus have high impact on viscosity, drying behavior, and other tactile and sensory characteristics of the formulation. Personal care compositions have a unique sensory feel that consumers come to recognize and love and associate with the particular brand or end-use. As the knowledge of the harmful effects of UV exposure developed, it became desirable to improve UV-A and UV-B protection substantially, without increasing levels of UV-A and UV-B protection. This is not trivial, particularly for non-solid personal care formulations, since sunscreens tend to have high impact on viscosity, drying behavior, and other tactile and sensory characteristics of the formulation. If the feel of the formulation is altered, consumer loyalty may quickly change. It is critical to preserve the sensory profile of the composition while achieving a substantial UV-A and UV-B boost.

The technology provided in the instant application unexpectedly delivers a significant boost in UV-A and UV-B protection, and in SPF, by virtue of incorporating certain non-aromatic carboxylic acids.

SUMMARY

In an aspect, a personal care composition is provided that includes about 0.1 wt % to about 10 wt % of

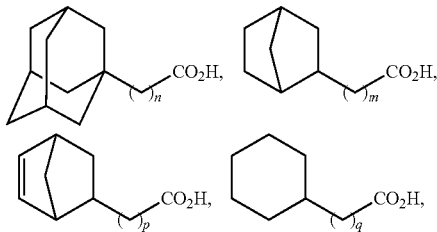

or salts thereof, or a mixture of any two or more thereof;
wherein n is 0, 1, or 2 and m, p, and q are each independently 1, 2, or 3;
about 0.1 wt % to about 30 wt % of a UV-B sunscreen oil;
about 0.1 wt % to about 30 wt % of a nonionic surfactant of Formula I

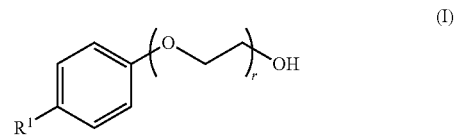

where $R^1$ is a $C_6$-$C_{12}$ alkyl group; r is an integer from 6 to 13, and the nonionic surfactant has a hydrophilic-lipophilic balance of about 10 to about 14; and
about 40 wt % to about 96 wt % of the personal care composition is water.

The personal care composition preferably includes about 0.1 wt % to about 10 wt % of

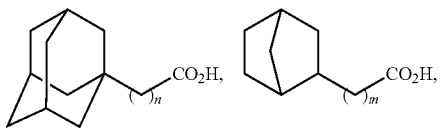

or salts thereof, or a mixture of any two or more thereof. In the any embodiment described herein, n is preferably 0 or 1, and n is most preferably 0. In the any embodiment described herein, m is preferably 1. $R^1$ of the nonionic surfactant of Formula I is preferably a $C_7$-$C_{10}$ alkyl group, most preferably a $C_8$ alkyl group. In the any embodiment described herein, r of Formula I is preferably an integer from 7 to 11; the hydrophilic-lipophilic balance is preferably about 11 to about 14.

The personal care composition may further include about 0.1 wt % to about 10 wt % of a UV-A sunscreen oil. The personal care composition may further include a water-insoluble cosmetic benefit ingredient.

The personal care composition may be in the form of a gel or sprayable, where the personal care composition includes about 60 wt % to about 96 wt % water.

The personal care composition of any of the above embodiments may be a vanishing cream, where the personal care composition further includes about 5 wt % to about 40 wt % fatty acid and about 0.1 wt % to about 20 wt % soap.

In a related aspect, a method of increasing SPF protection is provided, where the method includes applying to skin any one of the embodiments of the personal care composition described herein.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution.

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The term "personal care composition" as used herein, is meant to include a composition for topical application to the skin and/or hair of humans. Such a composition may be generally classified as leave-on or rinse off, and includes any product applied to a human body for also improving appearance, cleansing, odor control or general aesthetics. The personal care composition of the present technology can be in the form of a liquid, lotion, cream, foam, scrub, gel, spray, or toner, or applied with an implement or via a face mask, pad or patch. Non-limiting examples of such compositions include leave-on skin lotions, creams, antiperspirants, deodorants, foundations, mascara, sunless tanners, sunscreen lotions, spray-on sunscreens, and wash-off shampoos, conditioners, and shower gels. The personal care composition of the present technology is preferably a leave-on composition, and especially a leave-on skin care composition, because such compositions are the most challenging in terms of boosting UV-A/UV-B/SPF without increasing sunscreen oil amounts.

"Skin" as used herein is meant to include skin on the face and body (e.g., neck, chest, back, arms, underarms, hands, legs, buttocks, ears, and scalp). The composition of the present technology is also of relevance to applications on any other keratinous substrates of the human body other than skin, e.g., hair, where products may be formulated with specific aim of improving photoprotection.

Personal Care Compositions of the Present Technology

The present technology provides a personal care composition that includes about 0.1 wt % to about 10 wt % of a $C_8$-$C_{14}$ cycloalkylcarboxylic acid, a $C_8$-$C_{14}$ cycloalkylalkylcarboxylic acid, a $C_8$-$C_{14}$ cycloalkenylcarboxylic acid, a $C_8$-$C_{14}$ cycloalkenylalkylcarboxylic acid, or salts thereof, or a mixture of any two or more thereof (collectively, a "cyclocarboxylic acids and/or salts thereof"), such as

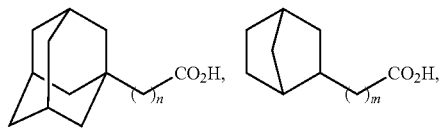

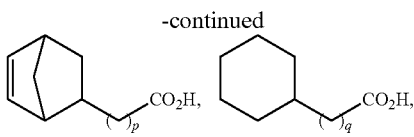

or salts thereof, or a mixture of any two or more thereof; where n is 0, 1, or 2; m is 1, 2, or 3; p is 1, 2, or 3; and q is 1, 2, or 3;

about 0.1 wt % to about 30 wt % of a UV-B sunscreen oil;
about 0.1 wt % to about 30 wt % of a nonionic surfactant of Formula I

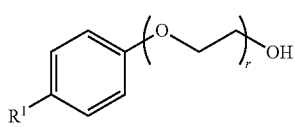

where $R^1$ is a $C_6$ alkyl group, a $C_7$ alkyl group, a $C_8$ alkyl group, a $C_9$ alkyl group, a $C_{10}$ alkyl group, a $C_{11}$ alkyl group, or a $C_{12}$ alkyl group; and r is 6, 7, 8, 9, 10, 11, 12, or 13, wherein the nonionic surfactant has a hydrophilic-lipophilic balance of about 10 to about 14; and about 40 wt % to about 96 wt % of the personal care composition is water (i.e., $H_2O$).

The personal care compositions are isotropic and/or homogeneous liquids that include microemulsions of the water-in-oil or oil-in-water type. Microemulsions are emulsions with a particle size of about 10 nm to about 200 nm; emulsions typically involve a emulsion particle sizes of greater than about 1000 nm, whereas micelles involve particle sizes of about 2 to about 5 nm. Such isotropic personal care compositions with microemulsions are well-suited for uniform coverage when applied to skin or hair. The personal care compositions may include multiple emulsions of the water-in-oil-in-water or oil-in-water-in-oil variety.

The personal care compositions of the present technology surprisingly exhibit SPF and UVAPF values significantly higher than similar compositions that do not possess a cyclocarboxylic acid of the present technology. Thus, the personal care compositions of the present technology exhibit enhanced photoprotection properties without needing to increase the sunscreen oil amounts in the composition. Without being bound by theory, it is believed the enhanced SPF and UVAPF values arise from both the microemulsions provided by the inclusion of one or more cyclocarboxylic acids as well as the uniform coverage provided by the personal care compositions of the present technology.

As disclosed above, the personal care composition includes about 0.1 wt % to about 10 wt % of a cyclocarboxylic acid (or salt thereof) of the present technology, where the amount may be about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.2 wt %, about 1.4 wt %, about 1.6 wt %, about 1.8 wt %, about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, about 3.8 wt %, about 4.0 wt %, about 4.2 wt %, about 4.4 wt %, about 4.6 wt %, about 4.8 wt %, about 5.0 wt %, about 5.5 wt %, about 6.0 wt %, about 6.5 wt %, about 7.0 wt %, about 7.5 wt %, about 8.0 wt %, about 8.5 wt %, about 9.0 wt %, about 10 wt %, or any range including and between any two of these values. For example, the amount of cyclocarboxylic acid may be about 0.1 wt % to about 6 wt %, preferably about 0.2 wt % to about 4 wt %, most preferably about 0.5 wt % to about 3 wt %. Useful salts of the cyclocarboxylic acids of the present technology include inorganic salts and organic salts. Inorganic salts include, but are not limited to, alkali metal and alkaline earth salts, such as sodium salts, potassium salts, magnesium salts, and calcium salts; ammonium ($NH_4^+$) salts; and aluminum salts. Examples of organic salts include, but are not limited to, alkyl ammonium (e.g., $CH_3CH_2NH_3^+$), aralkyl ammonium (e.g., $PhCH_2NH_3^+$) dialkyl ammonium (e.g., $(CH_3CH_2)_2NH_2^+$), diaralkyl ammonium, alkyl aryl ammonium, alkyl aralkyl ammonium (e.g., $(PhCH_2)(CH_3CH_2)NH_2^+$)), trialkyl ammonium, triaralkyl ammonium, alkyl diaryl ammonium, dialkyl aryl ammonium, tetraalkyl ammonium, tetraaralkyl ammonium, alkyl triaralkyl ammonium, dialkyl diaralkyl ammonium, and trialkyl aralkyl ammonium (e.g., $(CH_3)_3(PhCH_2)N^+$). Thus, the personal care composition may include one or more cyclocarboxylic acids as described above, one or more salts of any one of the above cyclocarboxylic acids, as well as mixtures of one or more cyclocarboxylic acids and one or more salts of any one of the above cyclocarboxylic acids.

The personal care composition preferably includes

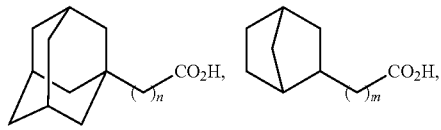

or salts thereof, or a mixture of any two or more thereof. In the any embodiment described herein, n is preferably 0 or 1, and n is most preferably 0. In any embodiment described herein, the cyclocarboxylic acid preferably includes one or more of adamantane-1-carboxylic acid (i.e., where n is 0), 2-norbornane acetic acid (bicyclo[2.2.1]heptane-2-carboxylic acid; i.e., where m is 1), norbornene carboxylic acid (bicyclo[2.2.1]hept-5-ene-2-carboxylic acid; i.e., where p is 0), cyclohexylacetic acid (2-cyclohexylacetic acid; i.e., where q is 1), and a salt of any one or more thereof.

The UV-B sunscreen oil may be selected from the class of cinnamic acid, salicylic acid, diphenyl acrylic acid, or derivatives thereof. The UV-B sunscreen oil may include one or more of octyl salicylate, 3,3,5-trimethylcyclohexyl 2-hydroxybenzoate, ethylhexyl salicylate, 2-ethylhexyl 2-cyano-3,3-diphenyl-2-propenoate, or 2-ethylhexyl-4-methoxycinnamate (also known as octyl methoxycinnamate or "OMC"). Such UV-B sunscreen oils are typically commercially available, such as Octisalate™ (octyl salicylate), Homosalate™ (3,3,5-trimethyleyclohexyl 2-hydroxybenzoate), NeoHeliopan™ (a range of organic UV filters including OMC (Neo Heliopan AV™) and ethylhexyl salicylate (Neo Heliopan OS™)), Octocrylene™ and Milestab 3039™ (2-ethylhexyl-2-cyano-3,3-diphenyl-2-propenoate) or Parsol MCX™ (2-ethylhexyl-4-methoxycinnamate). The amount of UV-B sunscreen oil in the personal care composition may be about 0.1 wt % to about 20 wt %, preferably about 0.2 wt % to about 10 wt %, more preferably about 0.5 wt % to about 7 wt %, most preferably about 2 wt % to about 6 wt %.

The personal care composition may further include a UV-B sunscreen that is water-soluble. The water soluble UV-B sunscreen may also include phenylbezimidazole sulfonic acid (also known as ensulizole), 4-aminobenzoic acid (also known as para-aminobenzoic acid or "PABA"), or both.

About 0.1 wt % to about 30 wt % of the personal care composition is a nonionic surfactant of Formula I with a hydrophilic-lipophilic balance of about 10 to about 14. Determining the hydrophilic-lipophilic balance is well understood by a person of ordinary skill in the art, as exemplified by Griffin W C. "Classification of Surface-Active Agents by 'HLB'." J. Soc. Cosmet. Chem. 1949; 1: 311-326; Griffin W C. "Calculation of HLB values of non-ionic surfactants." J. Soc. Cosmet. Chem. 1954; 5: 249-256; and "The HLB system—a time saving guide to emulsifier selection." CHEMMUNIQUE (Ed.), (1980). ICI Americas Inc. Delaware, USA. The amount of nonionic surfactant in the personal care composition may be about 0.2 wt %, to about 25 wt %, preferably about 1 wt % to about 20 wt %, most preferably about 1 wt % to about 15 wt %. The hydrophilic-lipophilic balance of the nonionic surfactant may be about 10, about 11, about 12, about 13, about 14, or any range including and between any two of these values. Preferably, the hydrophilic-lipophilic balance of the nonionic surfactant is from about 11 to about 14, more preferably from about 10.9 to about 13.9, and even more preferably from about 12.4 to about 13.5. Commercially available nonionic surfactants of Formula I with such hydrophilic-lipophilic balances include, but are not limited to, Triton X-100™, Triton X-II4™, Tergitol NP-6™, Tergitol NP-7™, Tergitol NP-8™, Tergitol NP-9™, Tergitol NP-10™, Tergitol NP-11™, Tergitol NP-12™, and Tergitol NP-13™ from Dow Chemical Company. $R^1$ of the nonionic surfactant of Formula I is preferably a $C_7$-$C_{10}$ alkyl group, most preferably a $C_8$ alkyl group. $R^1$ may be a multi-branched $C_6$-$C_{12}$ alkyl group, for example, a 2,4,4-trimethylpentan-5-yl group. r of Formula I is preferably an integer from 7 to 11.

The amount of water in the personal care composition is from about 40 wt % to about 96 wt %. The amount of water in the personal care composition may be about 60 wt % to about 95 wt %, and more preferably greater than 70 wt %.

The personal care composition of any one of the above embodiments may further include about 0.1 wt % to about 10 wt % of a UV-A sunscreen oil. The personal care compositions of the present technology that incorporate a UV-A sunscreen oil exhibit a significantly higher UVAPF when compared to compositions lacking the cyclocarboxylic acid. The UV-A sunscreen oil may include one or more of 4-t-butyl-4'-methoxydibenzoylmethane ("avobenzone"), 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxy-dibenzoylmethane, 2-methyl-5-tert-butyl-4'-methoxy-dibenzoylmethane, 2,4-dimethyl-4'-methoxydibenzoylmethane, 2,6-dimehyl-4-tert-butyl-4'-methoxy-dibenzoylmethane, diethylaminohydroxybenzoyl hexyl benzoate, ecamsule, or methyl anthranilate. The amount of UV-A sunscreen oil in the personal care composition may preferably be about 0.5 wt % to about 7 wt %, more preferably about 1 wt % to about 5 wt %.

Additional suitable sunscreen oils suitable for use in the personal care composition include those commercially available from BASF corporation: Uvinul T-150 (Ethylhexyl triazone; a UV-B sunscreen oil), Uvinul A Plus (Diethylamino hydroxybenzoyl hexyl benzoate; a UV-A sunscreen oil), Tinosorb S (bis-ethylhexyloxyphenol methoxyphenyl triazine; a UV-A and UV-B sunscreen oil), Tinosorb M(methylene bisbenzotriazolyl tetramethylbutylphenol; a UV-A and UV-B sunscreen oil). Bisdisulizone disodium may also be included in the personal care composition.

A particularly preferred combination of UV-A and UV-B sunscreen oils is avobenzone and 2-ethylhexyl-4-methoxycinnamate.

The personal care composition of any one of the embodiments described herein may further include a weight ratio of about 3.5:1 to about 20:1 of the UV-B & UV-A (when UV-A is present) sunscreen oils to the cyclocarboxylic acids. The personal care composition of any embodiment described herein may preferably include a weight ratio of the UV-B & UV-A sunscreen oils to the cyclocarboxylic acids of about 5:1 to about 14:1.

The personal care composition of any one of the embodiments described herein may further include a weight ratio of about 0.4:1 to about 5:1 of nonionic surfactant to combined weight of UV-B & UV-A sunscreen oils. The weight ratio of nonionic surfactant to combined weight of UV-B & UV-A sunscreen oils may preferably be about 0.5:1 to about 4:1, more preferably about 0.6:1 to about 3.5:1, and even more preferably about 0.85:1 to about 3:1.

The personal care composition of any one of the embodiments described herein may include a weight ratio of about 3.5:1 to about 20:1 of nonionic surfactant to cyclocarboxylic acid. The personal care composition of any embodiment described herein may preferably include a weight ratio of nonionic surfactant to cyclocarboxylic acid of about 5:1 to about 14:1.

In any embodiment of the personal care composition described herein, the combined weight of nonionic surfactant, UV-B sunscreen oil, and UV-A sunscreen oil may be about 3 wt % to about 60 wt %, preferably about 5% to about 30%, of the personal care composition.

The personal care compositions of any of the embodiments described herein may be clear or translucent composition, a beneficial property especially in light of the enhanced photoprotection properties exhibited and sunscreen oil amounts. Clear compositions are homogeneous solutions that are essentially free from visible particulates (essentially free here meaning <10 particles per liter) when viewed by a person without enhancement and with normal vision; translucent compositions are solutions that allow the passage of light through the solution and include particulates and/or ingredients with a different refractive index that causes light scattering. Such clear/translucent personal care compositions may include one or more of a weight ratio of about 3.6:1 to about 20:1 of the UV-B & UV-A (when UV-A is present) sunscreen oils to the cyclocarboxylic acids, a weight ratio of about 0.4:1 to about 5:1 of nonionic surfactant to combined weight of UV-B & UV-A sunscreen oils, a weight ratio of about 3.5:1 to about 20:1 of nonionic surfactant to cyclocarboxylic acid, acombined weight of nonionic surfactant, UV-B sunscreen oil, and UV-A sunscreen oil of about 3 wt % to about 60 wt % of the personal care composition, as well as any previously described preferable range thereof.

The personal care composition of any one of the above embodiments may further include a cosmetic benefit ingredient. Such cosmetic benefit ingredients include, but are not limited to, skin lightening ingredients, retinoids, herbal extracts, anti-fungal agents, resveratrol, alpha-lipoic acid, ellagic acid, kinetin, retinoxytrimethylsilane, ceramides, pseudoceramides, colorants, opacifiers, abrasives, and combinations of any two or more thereof.

The personal care composition of any embodiment described herein preferably includes a skin lightening ingredient. Illustrative skin lightening ingredients include, but are not limited to, placental extract, lactic acid, niacinamide, arbutin, kojic acid, ferulic acid, hydroquinone, resorcinol, resorcinol derivatives (including 4-substituted resorcinols, such as especially 4-hexyl. 4-ethyl, 4-butyl, and/or 4-isopropyl resorcinols), dicarboxylic acids, 12-hydroxystearic acid ("12HSA"), and combinations of any two or more thereof. The skin lightening ingredient preferably includes a tyrosinase inhibitor to complement the melanogenesis inhibition activity of the substituted monoamines, such as kojic acid, hydroquinone and a 4-substituted resorcinol. Dicarboxylic acid skin lightening ingredients include those represented by the formula $HOOC-(C_xH_y)-COOH$ where x is 4, 5, 6, 7, 8, 9, 10, 11, 12, 13, 14, 15, 16, 17, 18, 19, or 20, and y is 6, 8, 10, 12, 14, 16, 18, 20, 22, 24, 26, 28, 30, 32, 34, 36, 38, or 40, where such dicarboxylic acids include, but are not limited to, azelaic acid, sebacic acid, oxalic acid, succinic acid, fumaric acid, octadecenedioic acid, salts thereof, and mixtures of any to or more thereof. The amount of skin lightening ingredient may be about 0.1 wt % to about 10 wt %, or any range including and between these two values. For example, the amount of skin lightening ingredient is preferably from about 0.5 wt % to about 2 wt % of the personal care composition. It is further preferred that the skin lightening ingredient include a coactive such as vitamin $B_3$, a vitamin $B_3$ derivative, (e.g., niacinamide, nicotinic acid esters, non-vasodilating esters of nicotinic acid, nicotinyl amino acids, nicotinyl alcohol esters of carboxylic acids, nicotinic acid N-oxide, niacinamide N-oxide) or mixtures of any two or more thereof.

Another preferred cosmetic benefit ingredient is a retinoid. As used herein, "retinoid" includes all natural and/or synthetic analogs of vitamin A, or retinal-like compounds which possess the biological activity of vitamin A in the skin, as well as geometric isomers and stereoisomers of these compounds. The retinoid is preferably retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), more preferably retinoids other than retinoic acid. Such compounds are well known in the art and are commercially available from a number of sources, e.g., Sigma Chemical Company (St. Louis, Mo.), and Boerhinger Mannheim (Indianapolis, Ind.). Retinoids include those described in U.S. Pat. Nos. 4,677,120, 4,885,311, 5,049,584, 5,124,356, and U.S. Pat. No. Reissue 34,075, as well as tocopheryl-retinoate (the tocopherol ester of retinoic acid), adapalene (6-[3-(1-adamantyl)-4-methoxyphenyl]-2-naphthoic acid), and tazarotene (ethyl 6-[2-(4,4-dimethylthiochroman-6-yl)-ethynyl]nicotinate). Preferred retinoids include retinol, retinyl palmitate, retinyl acetate, retinyl propionate, retinal and combinations of any two or more thereof. The personal care compositions of the present technology may contain a safe and effective amount of the retinoid, such that the personal care composition is safe and effective for regulating keratinous tissue condition, preferably for regulating visible and/or tactile discontinuities in skin, more preferably for regulating signs of skin aging, even more preferably for regulating visible and/or tactile discontinuities in skin texture associated with skin aging. The compositions preferably contain from 0.005% to 2%, more preferably 0.01% to 2%, retinoid. Retinol is preferably used in about 0.01 wt % to about 0.15 wt %; retinol esters are preferably used in an amount of about 0.01 wt % to about 2 wt %; retinoic acids are preferably used in an amount of about 0.01% to about 0.25%; tocopheryl-retinoate, adapalene, and tazarotene are each preferably used in an amount of about 0.01% to about 2%.

A wide variety of herbal extracts are useful as cosmetic benefiting ingredients. Illustrative herbal extracts include pomegranate, white birch (Betula Alba), green tea, chamomile, licorice, extracts thereof, and combinations of any two or more thereof. The herbal extracts may either be water soluble or water-insoluble, carried in a solvent which respectively is hydrophilic or hydrophobic. Water and ethanol are the preferred extract solvents. The herbal extract may be about 0.000001 wt % to about 10 wt % of the personal care composition, preferably from 0.0001 wt % to about 1 wt %.

Anti-fungal agents suitable for inclusion in personal care compositions are well known to one of skill in the art. Examples include, but are not limited to, climbazole, ketoconazole, fluconazole, clotrimazole, miconazole, econazole, etaconazole, terbinafine, salts of any one or more of these (e.g., hydrochloride salts), zinc pyrithione, selenium disulfide, and combinations of any two or more thereof.

The personal care composition may also include one or more of resveratrol, alpha-lipoic acid, ellagic acid, kinetin, retinoxytrimethylsilane (available from Clariant Corp. under the Silcare 1M-75 trademark), dehydroepiandrosterone (DHEA), and combinations of any two or more thereof. Ceramides (including Ceramide 1, Ceramide 3, Ceramide 3B, Ceramide 6 and Ceramide 7) as well as pseudoceramides may also be included in any embodiment of the personal care composition described herein, but may also be excluded from any embodiment of the personal care composition described herein. Amounts of these materials may range from about 0.000001 wt % to about 10 wt % of the personal care composition, preferably from 0.0001 wt % to about 1 wt %.

Colorants, opacifiers and abrasives may also be included in the personal care composition of the present technology. Each of these substances may range from about 0.05 wt % to about 5 wt %, preferably from about 0.1 wt % to about 3 wt %, of the composition.

The personal care composition may further include about 0.1 wt % to about 8 wt % of a film forming polymer. Such film-forming polymers include, but are not limited to, polyalkyleneoxy terminated polyamides (e.g., INCI name: Polyamide-3, Polyamide-4), polyether polyamides (e.g., INCI name: Polyamide-6), mixed acid terminated polyamides (e.g., INCI name: Polyamide-7), and ester terminated poly (ester-amides) (e.g., INCI name: Polyamide-8). Such film forming polymers may be synthesized or are available commercially, such as under the Sylvaclear™ line of products by Arizona Chemical Company, LLC and the OleoCraft™ line of products by Croda International PLC. Film-forming polymers also include, but are not limited to, the INCI named Polyester-5 (e.g., Eastman AQ™ 38S Polymer), PPG-17/IPDI/DMPA Copolymer (e.g., Avalure™ UR 450 Polymer), Acrylates Copolymer (e.g., Avalure™ AC 120 Polymer), and polysaccharides such as Xilogel (tamarin gum), lotus bean gums, tara gum, beta glucan, pullulan, carboxymethyl cellulose, hydroxypropyl cellulose, sodium alginate, potato starch, carrageenan. The film forming polymer may include combinations of any two or more of the polymers recited above. The amount of film forming polymer in the personal care composition may be about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1.0 wt %, about 1.2 wt %, about 1.4 wt %, about 1.6 wt %, about 1.8 wt %, about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, about 3.8 wt %, about 4.0 wt %, about 4.2 wt %, about 4.4 wt %, about 4.6 wt %, about 4.8 wt %, about 5.0 wt %, about 5.2 wt %, about 5.4 wt %, about 5.6 wt %, about 5.8 wt %, about 6.0 wt %, about 6.2 wt %, about 6.4 wt %, about 6.6 wt %, about 6.8 wt %, about 7.0 wt %, about 7.2 wt %, about 7.4 wt %, about 7.6 wt %, about 7.8 wt %, about 8.0 wt % or any range including and between any two of these values. Preferable amounts of film forming polymer are about 1 wt % to about 3 wt %.

The personal care composition of any one of the embodiments described herein may further include a tricyclodecaneamide, including but not limited to those described in International Pub. No. WO 2014/139965, incorporated herein by reference in its entirety for any and all purposes. Preferred tricyclodecaneamides include, but are not limited to,

- (morphonyl)tricyclo[3.3.1.1$^{3.7}$]dec-1-yl-methanone;
- (piperidinyl)tricyclo[3.3.1.1$^{3.7}$]dec-1-yl-methanone;
- (pyrrolidinyl)tricyclo[3.3.1.1$^{3.7}$]dec-1-yl-methanone;
- (azetidinyl)tricyclo[3.3.1.1$^{3.7}$]dec-1-yl-methanone;
- (hexahydroazepinyl)tricyclo[3.3.1.1$^{3.7}$]dec-1-yl-methanone;
- (4-cyano-piperidinyl)tricyclo[3.3.1.1$^{3.7}$]dec-1-yl-methanone,
- (4-amido-piperidinyl)tricyclo[3.3.1.1$^{3.7}$]dec-1-yl-methanone;
- (tricyclo[3.3.1.1$^{3.7}$]decanyl)-N-tricyclo[3.3.1.1$^{3.7}$]dec-1-yl-methanone;
- (decahydroisoquinolinyl)tricyclo[3.3.1.1$^{3.7}$]dec-1-yl-methanone;
- (decahydroquinolinyl)tricyclo[3.3.1.1$^{3.7}$]dec-1-yl-methanone;
- (3,3-dimethyl-1-piperidinyl)tricyclo[3.3.1.1$^{3.7}$]dec-1-yl-methanone;
- (2-methyl-1-piperidinyl)tricyclo[3.3.1.1$^{3.7}$]dec-1-yl-methanone;
- (4-methyl-1-piperidinyl)tricyclo[3.3.1.1$^{3.7}$]dec-1-yl-methanone;
- (3-methyl-1-piperidinyl)tricyclo[3.3.1.1$^{3.7}$]dec-1-yl-methanone;
- (3,5-dimethyl-1-piperidinyl)tricyclo[3.3.1.1$^{3.7}$]dec-1-yl-methanone;
- (4-methyl-4-ethy-piperidinyl)tricyclo[3.3.1.1$^{3.7}$]dec-1-yl-methanone;
- (3,3-diethyl-1-pyrrolidinyl)tricyclo[3.3.1.1$^{3.7}$]dec-1-yl-methanone;
- (N,N-diisopropyl)tricyclo[3.3.1.1$^{3.7}$]dec-1-yl-methanone;
- (3,3-dimethylbutylaminyl)tricyclo[3.3.1.1$^{3.7}$]dec-1-yl-methanone;
- (2,2-dimethylpropylaminyl)tricyclo[3.3.1.1$^{3.7}$]dec-1-yl-methanone;
- (1, 1-dimethyl-3,3-dimethylbutylaminyl)tricyclo[3.3.1.1$^{3.7}$]dec-1-yl-methanone; and
- (1,3-dimethyl-butylaminyl)tricyclo[3.3.1.1$^{3.7}$]dec-1-yl-methanone.

The amount of tricyclodecaneamide may be included from about 0.0001 wt % to about 20 wt % of the personal care composition, or any range between these values. For example, the amount of tricyclodecaneamide may preferably be from about 0.001 wt % to about 10 wt %; more preferably from about 0.01 wt % to about 5 wt %, and most preferably from about 0.5 wt % to about 10 wt % of the personal care composition.

The personal care composition may be at a pH of about 4 to about 8. The pH of the personal care composition may be about 4, about 4.5, about 5, about 5.5, about 6, about 6.5, about 7, about 7.5, about 8, or any range including and between any two of these values. For example, the pH of the personal care composition is preferably from about 5 to about 7, and most preferably from about 5 to about 6.

The personal care composition of any one of the embodiments described herein may further include an inorganic sunscreen. The amount of inorganic sunscreen may be from about 0.1 wt % to about 10 wt % of the personal care composition or any range between these values. Inorganic sunscreens are well known to one of ordinary skill in the art and include, but are not limited to, zinc oxide, iron oxide, silica (e.g., fumed silica), and titanium dioxide.

The personal care composition of any one of the above embodiments may be in the form of a gel and/or may be sprayable. Spray forms of personal care compositions are especially difficult when high SPF and UVAPF is desired because incorporation of oils is difficult and limited at the high water concentrations required. However, the sprayable personal care compositions of the present technology provide desirable SPF and UVAPF values. When in a gel or sprayable form, the personal care composition includes about 60 wt % to about 96 wt % water, and preferably greater than about 70 wt % water. Gel or sprayable forms of the personal care composition preferably include about 0.1 wt % to about 5 wt % of the film forming polymers previously described, or any previously described range in between these two values. Such gel or sprayable forms may be clear or translucent as described herein.

The personal care of any one of the above embodiments may be a vanishing cream. When a vanishing cream, the personal care composition further includes about 5 wt % to about 40 wt % fatty acid and about 0.1 wt % to about 20 wt % soap. Fatty acids having from 10 to 30 carbon atoms are suitable for incorporation into such vanishing creams, where illustrative examples include pelargonic acid, lauric acid, myristic acid, palmitic acid, stearic acid, isostearic acid, oleic acid, linoleic acid, linolenic acid, hydroxystearic acid, and behenic acids, and mixtures of any two or more thereof. The soap may be the lithium salt, sodium salt, potassium salt, or mixture of any two or more thereof, of the fatty acid(s) of the vanishing cream, where the soap preferably includes a potassium salt. Particularly preferred are compositions that include higher than about 7 wt %, more preferably higher than about 10 wt %, and most preferably higher than about 12 wt % fatty acid.

The fatty acid preferably includes a mixture of stearic acid and palmitic acid and the soap is preferably the potassium salt of the fatty acid mixture, although other counterions and mixtures thereof may be used. The fatty acid in vanishing cream is often prepared using hystric acid which is generally about 90 to 95% a mixture of stearic acid and palmitic acid. A typical hystric acid includes about 52-55 wt % palmitic acid and about 45-48 wt % stearic acid of the total palmitic-stearic mixture.

The personal care compositions of the present technology may include a cosmetically acceptable carrier in addition to water. Such carriers include, but are not limited to, emollients, fatty acids, fatty alcohols, thickeners, and combinations of any two or more thereof.

Emollients may be silicone oils, natural or synthetic esters, hydrocarbons, alcohols, fatty acids, and combinations of any two or more thereof. Amounts of the emollients may be about 0.1 wt % to about 60 wt % of the personal care composition, preferably about 30 wt % to about 50 wt %.

Silicone oils may be divided into the volatile and non-volatile variety. The term "volatile" as used herein refers to those materials which have a measurable vapor pressure at ambient temperature. Volatile silicone oils are preferably chosen from cyclic polydimethylsiloxanes (cyclomethicones) or linear polydimethylsiloxanes containing from 3, 4, 5, 6, 7 8, or 9 silicon atoms, preferably from 5 to 6 silicon atoms. Nonvolatile silicone oils include polyalkyl siloxanes, polyalkylaryl siloxanes, and polyether siloxane copolymers. Nonvolatile polyalkyl siloxanes useful herein include, for example, polydimethyl siloxanes with viscosities from about $5 \times 10^{-6}$ m$^2$/s to about 0.1 m$^2$/s at 25° C., preferably from about $1 \times 10^{-6}$ m$^2$/s to about 4×10-4 m$^2$/s at 25° C. Other classes of nonvolatile silicones are emulsifying and non-emulsifying silicone elastomers, such as DimethiconeNinyl Dimethicone Crosspolymer (available as Dow Corning 9040, General Electric SFE 839, and Shin-Etsu KSG-18). Silicone waxes, such as Silwax WS-L (Dimethicone Copolyol Laurate), may also be included in any one of the embodiments of the personal care compositions described herein.

Ester emollients include, but are not limited to:
a) Alkyl esters of saturated fatty acids having 10 to 24 carbon atoms. Examples thereof include behenyl neopentanoate, isononyl isonanonoate, isopropyl myristate and octyl stearate;
b) Ether-esters (such as fatty acid esters) of ethoxylated saturated fatty alcohols;
c) Polyhydric alcohol esters, such as ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols;
d) Wax esters such as beeswax, spermaceti wax and tribehenin wax; and
e) Sugar esters of fatty acids, such as sucrose polybehenate and sucrose polycottonseedate.

Natural ester emollients principally are based upon mono-, di- and tri-glycerides. Representative examples include sunflower seed oil, coconut oil, cottonseed oil, borage oil, borage seed oil, primrose oil, castor and hydrogenated castor oils, rice bran oil, soybean oil, olive oil, safflower oil, shea butter, jojoba oil and combinations of any two or more thereof. Animal-derived emollients include, for example, lanolin oil and lanolin derivatives. Preferably, the amount of the natural ester is from about 0.1 wt % to about 20 wt % of the personal care composition.

Hydrocarbons which are suitable cosmetically acceptable carriers include petrolatum, mineral oil, $C_{11}$-$C_{13}$ isoparaffins, polybutenes, and especially isohexadecane (available commercially as Permethyl 101A from Presperse Inc.).

Fatty acids having from 10 to 30 carbon atoms are also suitable cosmetically acceptable carriers. Illustrative of this category are pelargonic, lauric, myristic, palmitic, stearic, isostearic, oleic, linoleic, linolenic, hydroxystearic and behenic acids, and mixtures of any two or more thereof.

Fatty alcohols having from 10 to 30 carbon atoms are another useful category of cosmetically acceptable carrier. Illustrative of this category are stearyl alcohol, lauryl alcohol, myristyl alcohol, oleyl alcohol, cetyl alcohol, and mixtures of any two or more thereof.

Preferred are emollients, especially for products intended to be applied to the face, that improve sensory properties and include oils that do not form stiff gels with 12HSA; these include polypropylene glycol-14 butyl ether ("PPG-14 butyl ether"; commercially available as Tegosoft PBE), or polypropylene glycol-15 stearyl ether ("PPG15 stearyl ether"; commercially available as Tegosoft E), oils such as castor oils and derivatives thereof, esters such as isopropyl myristate and isopropyl palmitate, as well as combinations of any two or more thereof.

Typical thickeners include crosslinked acrylates (e.g., Carbopol 982®), hydrophobically-modified acrylates (e.g., Carbopol 1382®), polyacrylamides (e.g., Sepigel 305®), acryloylmethylpropane sulfonic acid/salt polymers and copolymers (e.g., Aristoflex HMB® and AVC®), cellulosic derivatives, natural gums, and combinations of any two or more thereof. Among useful cellulosic derivatives are sodium carboxymethylcellulose, hydroxypropyl methocellulose, hydroxypropyl cellulose, hydroxyethyl cellulose, ethyl cellulose, hydroxymethyl cellulose, and combinations of any two or more thereof. Natural gums include, but are not limited to, guar, xanthan, sclerotium, carrageenan, pectin, and combinations of any two or more thereof. Inorganics may also be utilized as thickeners, particularly clays such as bentonites and hectorites, fumed silicas, talc, calcium carbonate and silicates such as magnesium aluminum silicate (Veegum®), as well as combinations of any two or more of these organics. Combinations of any two or more thickeners are also useful in the personal care compositions of the present technology. Amounts of the thickener may range from about 0.0001 wt % to about 10 wt %, preferably about 0.001 wt % to about 1 wt %, and optimally may be from about 0.01 wt % to about 0.5 wt % of the personal care composition.

Humectants of the polyhydric alcohol-type may be employed as cosmetically acceptable carriers. Typical polyhydric alcohols include, but are not limited to, glycerol, polyalkylene glycols (more preferably alkylene polyols and their derivatives, including propylene glycol, dipropylene glycol, polypropylene glycol, polyethylene glycol and derivatives thereof), sorbitol, hydroxypropyl sorbitol, hexylene glycol, 1,3-butylene glycol, isoprene glycol, 1,2,6-hexanetriol, ethoxylated glycerol, propoxylated glycerol, and mixtures of any two or more thereof. The amount of humectant may range anywhere from about 0.5 wt % to about 50 wt % of the personal care composition. The amount of humectant in the personal care composition may be about 0.5 wt % to about 50 wt %. Preferably, when a humectant is included, it is included in an amount of about 1 wt % and 15 wt % of the personal care composition.

Skin moisturizers may be included as a cosmetically acceptable carrier. Hyaluronic acid and/or its precursor N-acetyl glucosamine are both skin moisturizers that may be included, where N-acetyl glucosamine may be found in shark cartilage or shiake mushrooms and are available commercially from Maypro Industries, Inc (New York). Other preferred skin moisturizers include hydroxypropyl tri($C_1$-$C_3$ alkyl)ammonium salts. Such salts may be obtained in a variety of synthetic procedures, including hydrolysis of chlorohydroxypropyl tri($C_1$-$C_3$ alkyl)ammonium salts. A most preferred species is 1,2-dihydroxypropyltrimonium chloride, wherein each $C_1$-$C_3$ alkyl is a methyl group. Each $C_1$-$C_3$ alkyl constituent on the quaternized ammonium group may independently be methyl, ethyl, n-propyl, isopropyl, or hydroxyethyl. Particularly preferred is a trimethyl ammonium group known through INCI nomenclature as a "trimonium" group. Any anion may be included in the salt. The anion may be organic or inorganic with proviso that the material is cosmetically acceptable. Typical inorganic anions include halides, sulfates, phosphates, nitrates and borates. Most preferred are the halides, especially chloride. Organic anions include methosulfate, toluoyl sulfate, acetate, citrate, tartrate, lactate, gluconate, and benzenesulfonate. Still other preferred moisturizing agents, especially when used in conjunction with the aforementioned ammonium salts, include substituted ureas such as hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra(hydroxymethyl) urea; tetra(hydroxyethyl) urea; tetra(hydroxypropyl) urea; N-methyl-N'-hydroxyethyl urea; N-ethyl-N'-hydroxyethyl urea; N-hydroxypropyl-N'-hydroxyethyl urea, N,N'-dimethyl-N-hydroxyethyl urea. The "hydroxypropyl" group discussed includes 3-hydroxy-n-propyl, 2-hydroxy-n-propyl, 3-hydroxy-i-propyl, and 2-hydroxy-i-propyl. Most preferred is hydroxyethyl urea. The latter is available as a 50% aqueous liquid from the National Starch & Chemical Division of ICI under the trademark Hydrovance. The amount of substituted urea in the personal care composition may be about 0.01 wt % to about 20 wt %, preferably about 0.5 wt % to about 15 wt %, and most preferably about 2 wt % to about 10 wt %.

The personal care composition may include about 0.01 wt % to about 30 wt % of skin moisturizers. For example, the amount of ammonium salt may preferably be from about 0.2 wt % to about 30 wt %, about 0.5 wt % to about 20 wt %, and optimally from about 1 wt % to about 12 wt % of the personal care composition; the amounts of substituted urea may be from about 0.01 wt % to about 20 wt %, preferably from about 0.5 wt % to about 15 wt %, and most preferably from about 2 wt % to about 10 wt %.

When an ammonium salt and substituted urea are included together, in a preferred embodiment about 0.01 wt % to about 25 wt % of humectant (e.g., glycerine) is also included, preferably from about 0.2 wt % to about 20 wt %, and most preferably from about 1 wt % to about 15 wt %.

Preservatives may be included in the personal care composition of the present technology to protect against the growth of potentially harmful microorganisms. Suitable traditional preservatives include alkyl esters of para-hydroxybenzoic acid; other preservatives include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives include iodopropynyl butyl carbamate, phenoxyethanol, caprylyl glycol, $C_1$-$C_6$ alkyl parabens (especially, methyl paraben and/or propyl paraben), imidazolidinyl urea, sodium dehydroacetate, benzyl alcohol, and combinations of any two or more thereof. An especially preferred combination is octocrylene and caprylyl glycol, since caprylyl glycol has been disclosed to enhance UV-A and UV-B protection. The preservatives should be selected having regard for the use of the composition and possible incompatibilities between the preservatives and other ingredients in the emulsion, as is well understood by a person of ordinary skill in the art. Preservatives are preferably employed in amounts about 0.01 wt % to about 2 wt %.

A rheology modifier may further be included in any one of the embodiments of the personal care composition described herein. Such rheology modifiers include, but are not limited to, silica (such as fumed silica and hydrophilic silicas), clays (such as magnesium aluminum silicate, betonites, hectorite, and laponite), and mixtures of any two or more thereof. The rheology modifier may be included in an amount of about 0.01 wt %, to about 2.0 wt %. Preferably from about 0.05 wt % to about 1 wt % of the rheology modifier is included when present in the personal care composition.

The personal care compositions of the present technology are preferably non-solid. The personal care compositions of the present technology are preferably leave-on compositions. Leave-on compositions are to be distinguished from compositions which are applied to the skin and subsequently removed either by washing, rinsing, wiping, or the like either after or during the application of the personal care composition. Surfactants typically used for rinse-off compositions have physico-chemical properties giving them the ability to generate foam/lather in-use with ease of rinse; they may include mixtures of anionic, cationic, amphoteric, and nonionic surfactants. Surfactants used in leave-on compositions on the other hand are not required to have such properties as leave-on compositions are not intended to be rinsed-off. Leave-on compositions preferably include anionic surfactants no more than about 10 wt %, more preferably below about 8%, most preferably at most about 5 wt %, and optimally at most about 3 wt %.

The personal care compositions of the present technology may include a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the personal care compositions of the present technology. Examples include antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

In a related aspect, a method of increasing SPF protection is provided where the method includes applying to skin or hair any one of the above embodiments of the personal care composition. The applying step may include spreading and/or rubbing the personal care composition on the skin or hair. The applying step may include spraying the personal care composition on the skin or hair.

The examples herein are provided to illustrate advantages of the present technology and to further assist a person of ordinary skill in the art with preparing or using the compounds of the present technology or salts, pharmaceutical compositions, derivatives, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

In vitro SPF measurement was performed using an Optometric 290S SPF meter. Personal care compositions were each applied at a dosage of 2 mg/cm$^2$ on a PMMA (polymethylmethacrylate) plate or a glass plate (7 cm×7 cm) and allowed to air dry for 30 minutes at 22° C. The average SPF value was obtained from 6 SPF readings per plate. Two duplicated runs, the standard deviation from the average was ±2 SPF units. The % increase of in vitro SPF versus control is calculated as follows: [(measured SPF for selected formulation−measured SPF of control)/measured SPF of control]*100%. The % increase of in vitro UVAPF versus control is calculated as follows: [(measured UVAPF for selected formulation−measured UVAPF of control)/measured UVAPF of control]*100%.

Personal care compositions according to the present technology were compared to a control composition that did not incorporate a cyclocarboxylic acid of the present technology. Table 1 shows that while the control formulation exhibited good SPF and UVAPF values, Composition 1 exhibited a SPF increase of about 34% and a UVAPF increase of about 155% over the Control.

TABLE 1

| Composition (in H$_2$O) | SPF | UVAPF |
|---|---|---|
| 14% EHS, 14% TX100, 2% Avo | 70 | 64 |
| 14% EHS, 14% TX100, 2% Avo, 2% ACA | 94 | 163 |
| 14% EHS, 14% TX100, 4% Avo, 2% ACA | 140 | 465 |

EHS = ethylhexyl salicyclate
TX100 = Triton X-100
Avo = Avobenzone
ACA = adamantane-1-carboxylic acid SPF and UVAPF Increase in Vanishing Creams An exemplary vanishing cream personal care composition according to the present technology was generated with adamantane-1-carboxylic acid as the cyclocarboxylic acid ("ACA VC") and compared with a control composition that lacked a cyclocarboxylic acid ("Control VC"). The compositions of these vanishing creams are shown below in Table 2.

TABLE 2

| Component | Control VC | ACA VC |
|---|---|---|
| Stearic Acid | 17 wt % | 17 wt % |
| Cetyl Alcohol | 0.53 wt % | 0.53 wt % |
| Methyl Paraben | 0.2 wt % | 0.2 wt % |
| Glycerin | 1.0 wt % | 1.0 wt % |
| Potassium Hydroxide (KOH, 50%) | 0.96 wt % | 0.96 wt % |
| Disodium EDTA | 0.04 wt % | 0.04 wt % |
| Dimethicone | 0.5 wt % | 0.5 wt % |
| Propyl Paraben | 0.1 wt % | 0.1 wt % |
| Isopropyl Myristate | 0.75 wt % | 0.75 wt % |
| Aculyn 28 ™ | 2.0 wt % | 2.0 wt % |
| 2-ethylhexyl-4-methoxycinnamate (OMC) | 4.0 wt % | 4.0 wt % |
| Avobenzone | 1.5 wt % | 1.5 wt % |
| Triton X-100 | 1.5 wt % | 1.5 wt % |
| Niacinamide | 1.25 wt % | 1.25 wt % |
| Phenoxyethanol | 0.4 wt % | 0.4 wt % |
| Adamantane-1-carboxylic acid (ACA) | — | 0.2 wt % |
| DI Water | q.s | q.s |

In vitro assessment of the SPF and UVAPF exhibited by each vanishing cream was performed, with the results shown in Table 3. Table 3 illustrates that the vanishing cream of the present technology, ACA VC, significantly increased SPF (48% increase) and UVAPF (59% increase) over the Control VC.

TABLE 3

| Formulation | SPF | UVAPF |
|---|---|---|
| Control VC | 40 | 19 |
| ACA VC | 59 | 30 |

Personal Care Compositions Suitable for Spray/Gel Base Formulations

Clear/translucent formulations that are also suitable for gel or spray forms of personal care compositions were generated according to Table 4 below ("ACA Spray 1 & "ACA Spray 2") as well as a control formulation ("Control") that did not include a cyclocarboxylic acid of the present technology.

TABLE 4

| Components | Control | ACA Spray 1 | ACA Spray |
|---|---|---|---|
| Triton X-100 | 10.00 wt % | 10.00 wt % | 10.00 wt % |
| OMC | 2.40 wt % | 2.40 wt % | 2.40 wt % |
| Avobenzone | 1.00 wt % | 1.00 wt % | 1.00 wt % |
| ACA | 0.00 wt % | 0.50 wt % | 0.50 wt % |
| Butylene glycol | 4.00 wt % | 4.00 wt % | 4.00 wt % |
| glycerin | 5.00 wt % | 5.00 wt % | 5.00 wt % |
| Aristoflex AVC | 1.00 wt % | 1.00 wt % | 1.00 wt % |
| Sylvaclear WF1500V | 0.00 wt % | 0.00 wt % | 2.00 wt % |
| Water | 76.60 | 76.10 | 74.10 |

ACA = adamantane-1-carboxylic acid

The SPF and UVAPF properties of each formulation were examined, where Table 5 provides the results of the study. Table 5 evidences that the personal care compositions of the present technology exhibited higher SPFs and UVAPFs in comparison with the control formulation that did not include a cyclocarboxylic acid of the present technology.

TABLE 5

| Formulation | SPF | UVAPF |
|---|---|---|
| Control | 20 | 9 |
| ACA Spray 1 | 30 | 14 |
| ACA Spray 2 | 37 | 19 |

Tables 6-13 below provide exemplary personal care compositions of the present technology that are suitable for use as or incorporation into gel and spray forms. All percents are weight percents of the total composition. The "clear/translucent" property of the compositions was determined by the visual evaluation of a person with normal vision.

TABLE 6

Compositions including adamantane-1-carboxylic acid (ACA) and 2-ethylhexyl-4-methoxycinnamate (OMC)

| Triton X-100 | OMC | ACA | Water | Clear/translucent |
|---|---|---|---|---|
| 14.0% | 10.5% | 2.0% | 73.4% | yes |
| 14.0% | 12.6% | 2.0% | 71.3% | yes |
| 21.0% | 14.0% | 2.0% | 63.0% | yes |
| 28.0% | 14.0% | 2.0% | 56.0% | yes |
| 35.0% | 14.0% | 2.0% | 49.0% | yes |
| 2.3% | 2.3% | 0.3% | 95.1% | yes |
| 3.5% | 3.5% | 0.5% | 92.5% | yes |
| 7.0% | 7.0% | 1.0% | 85.0% | yes |
| 21.5% | 21.5% | 3.2% | 53.7% | yes |
| 24.1% | 24.1% | 3.6% | 48.2% | yes |
| 27.4% | 27.4% | 4.1% | 41.0% | yes |
| 14.0% | 7.0% | 2.0% | 63.0% | no |
| 1.4% | 1.4% | 0.2% | 97.0% | no |

TABLE 6-continued

Compositions including adamantane-1-carboxylic acid (ACA) and 2-ethylhexyl-4-methoxycinnamate (OMC)

| Triton X-100 | OMC | ACA | Water | Clear/translucent |
|---|---|---|---|---|
| 31.7% | 31.7% | 4.8% | 31.7% | no |
| 31.7% | 31.7% | 4.1% | 32.6% | no |
| 14.0% | 35% | 2.0% | 49.0% | no |
| 14.0% | 21% | 2.0% | 37.0% | no |
| 14.0% | 17.5% | 2.0% | 33.5% | no |

TABLE 7

Compositions including ACA, Ethylhexyl salicylate (EHS), and Avobenzone

| Triton x-100 | EHS | ACA | Water | Avobenzone | Clear/translucent |
|---|---|---|---|---|---|
| 14.0% | 14.0% | 2.0% | 68.0% | 2.0% | yes |
| 14.0% | 14.0% | 2.0% | 66.0% | 4.0% | yes |
| 2.3% | 2.3% | 0.3% | 95.1% | 0.3% | yes |

EHS = Ethylhexyl salicylate

TABLE 8

Composition including ACA, OMC, and Avobenzone

| Triton x-100 | OMC | ACA | Water | Avobenzone | Clear/translucent |
|---|---|---|---|---|---|
| 14.0% | 14.0% | 2.0% | 69.0% | 1.0% | yes |

OMC: 2-ethylhexyl-4-methoxycinnamate

TABLE 9

Compositions including EHS, 2-norbornane acetic acid (NorAA), and Avobenzone

| Triton x-100 | EHS | NorAA | Water | Avobenzone | Clear/translucent |
|---|---|---|---|---|---|
| 14.0% | 14.0% | 2.0% | 68.0% | 2.0% | yes |
| 14.0% | 14.0% | 2.0% | 66.0% | 4.0% | yes |
| 2.3% | 2.3% | 0.3% | 95.1% | 0.3% | yes |

NorAA = 2-norbornane acetic acid

TABLE 10

Composition including cyclohexylacetic acid (CHAA), EHS, and Avobenzone

| Triton x-100 | EHS | CHAA | Water | Avobenzone | Clear/translucent |
|---|---|---|---|---|---|
| 14.0% | 14.0% | 2.0% | 68.0% | 2.0% | yes |

CHAA = Cyclohexylacetic acid

TABLE 11

Composition including octocrylene

| Triton x-100 | EHS | ACA | Water | OCR | Clear/translucent |
|---|---|---|---|---|---|
| 16.9% | 13.5% | 2.0% | 65.6% | 2.0% | yes |

OCR = Octocrylene

TABLE 12

Composition including climbazole

| Triton x-100 | EHS | ACA | Water | Climbazole | Clear/translucent |
|---|---|---|---|---|---|
| 17.5% | 10.5% | 2.0% | 66.0% | 4.0% | yes |

TABLE 13

Composition including isopropyl myristate (IPM)

| Triton x-100 | EHS | ACA | Water | IPM | Clear/translucent |
|---|---|---|---|---|---|
| 22.0% | 16.6% | 2.0% | 55.4% | 4.0% | yes |

IPM = isopropyl myristate

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A personal care composition comprising
   a) about 0.1 wt % to about 10 wt % of

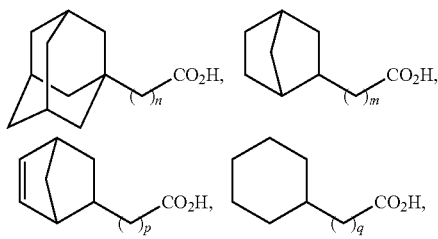

or salts thereof, or a mixture of any two or more thereof; wherein n is 0, 1, or 2; and m is 2 or 3; and p and q are each independently 1, 2, or 3;
   b) about 0.1 wt % to about 30 wt % of a UV-B sunscreen oil;
   c) about 0.1 wt % to about 30 wt % of a nonionic surfactant of formula I

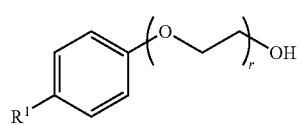

wherein
   $R^1$ is a $C_6$-$C_{12}$ alkyl group;
   r is an integer from 6 to 13; and
   wherein the nonionic surfactant has a hydrophilic-lipophilic balance of about 10 to about 14; and
   d) about 40 wt % to about 96 wt % $H_2O$.

2. The personal care composition of claim 1, wherein the UV-B sunscreen oil comprises one or more of octyl salicylate, 3,3,5-trimethylcyclohexyl 2-hydroxybenzoate, ethylhexyl methoxycinnamate, ethylhexyl salicylate, 2-ethylhexyl 2-cyano-3,3-diphenyl-2-propenoate, or 2-ethylhexyl-4-methoxycinnamate.

3. The personal care composition of claim 1, further comprising about 0.1 wt % to about 10 wt % of a UV-A sunscreen oil.

4. The personal care composition of claim 3, wherein the UV-A sunscreen oil comprises one or more of 4-t-butyl-4'-methoxydibenzoylmethane, 2-methyldibenzoylmethane, 4-methyl-dibenzoyl-ethane, 4-isopropyldibenzoyl-methane, 4-tert-butyldibenzoylmethane, 2,4-dimethyldibenzoylmethane, 2,5-dimethyldibenzoylmethane, 4,4'-di isopropyldibenzoylmethane, 2-methyl-5-isopropyl-4'-methoxy-dibenzoylmethane, 2-methyl-5-tert-butyl-4'-methoxydibenzoylmethane, 2,4-dimethyl-4'-methoxydibenzoylmethane, 2,6-dimehyl-4-tert-butyl-4'methoxy-dibenzoylmethane, bisdisulizone disodium, diethylaminohydroxybenzoyl hexyl benzoate, ecamsule, or methyl anthranilate.

5. The personal care composition of claim 1, wherein the composition further comprises a cosmetic benefit ingredient.

6. The personal care composition of claim 1, wherein $R^1$ of formula I is a multi-branched $C_6$-$C_{12}$ alkyl group.

7. The personal care composition of claim 1, wherein the nonionic surfactant has a hydrophilic-lipophilic balance of about 12.4 to about 13.5.

8. The personal care composition of claim 1, further comprising about 0.1 wt % to about 8 wt % of a film forming polymer.

9. The personal care composition of claim 1, further comprising a skin lightening ingredient.

10. The personal care composition of claim 1, further comprising a tricyclodecaneamide.

11. The personal care composition of claim 1, wherein the personal care composition is at a pH of from about 5 to about 6.

12. The personal care composition of claim 1, further comprising an inorganic sunscreen.

13. The personal care composition of claim 1, wherein
   the personal care composition comprises about 60 wt % to about 96 wt % $H_2O$; and
   is in the form of a gel or is sprayable.

14. The personal care composition of claim 1, wherein
   the personal care composition further comprises
      about 5 wt % to about 40 wt % fatty acid;
      about 0.1 wt % to about 20 wt % soap; and
   the personal care composition is a vanishing cream.

15. A method of increasing SPF protection, the method comprising applying to skin a composition of claim 1.

16. A method of increasing SPF of a sunscreen composition comprising:
(i) providing a sunscreen oil having a measurable SPF;
(ii) boosting said measurable SPF by including a non-aromatic carboxylic acid and nonionic surfactant of formula I as claimed in claim 1.

* * * * *